US00PP16607P3

(12) United States Plant Patent
Redman

(10) Patent No.: US PP16,607 P3
(45) Date of Patent: Jun. 6, 2006

(54) ***CHRYSANTHEMUM* PLANT NAMED 'FESTIVAL TIME YELLOW IMPROVED'**

(50) Latin Name: *Chrysanthemum morifolium*
Varietal Denomination: Festival Time Yellow Improved

(75) Inventor: Ruth Redman, Bognor Regis (GB)

(73) Assignee: Cleangro, Ltd., Chichester (GB)

( * ) Notice: Subject to any disclaimer, the term of this patent is extended or adjusted under 35 U.S.C. 154(b) by 122 days.

(21) Appl. No.: 10/993,260

(22) Filed: Nov. 18, 2004

(65) Prior Publication Data

US 2005/0114965 P1 May 26, 2005

Related U.S. Application Data

(60) Provisional application No. 60/524,335, filed on Nov. 20, 2003.

(51) Int. Cl.
*A01H 5/00* (2006.01)

(52) U.S. Cl. ..... Plt./289
(58) Field of Classification Search ..... Plt./289

See application file for complete search history.

(56) References Cited

U.S. PATENT DOCUMENTS

PP10,800 P 2/1999 Wain ..... Plt./78

OTHER PUBLICATIONS

2001 Ficor catalog, listing the variety 'Festival Time Yellow'. See, e.g., pp. 4 and 9.
2002 Ficor catalog, listing the variety 'Festival Time Yellow'. See, e.g., pp. 4 and 9.
2003 Ficor catalog, listing the variety 'Festival Time Yellow'. See, e.g., pp. 2, 3 and 7.
2002 Van Zanten North America catalog, listing the variety 'Festival Time Yellow'. See, e.g., p. 5 (photograph) and 6.

*Primary Examiner*—Anne Marie Grunberg
*Assistant Examiner*—Annette H Para
(74) *Attorney, Agent, or Firm*—Winston & Strawn, LLP

(57) ABSTRACT

A new variety of *Chrysanthemum* plant named 'Festival Time Yellow Improved,' having a dome capitulum of golden yellow decorative flowers with a contrasting orange center. The new variety 'Festival Time Yellow Improved' has an even branching habit with a good foliage presentation.

1 Drawing Sheet

Latin name of the genus and species: Botanical classification: *Chrysanthemum morifolium.*

Variety denomination: The new *Chrysanthemum* variety denomination is 'Festival Time Yellow Improved.'

BACKGROUND OF THE INVENTION

The present invention comprises a new and distinct cultivar of *Chrysanthemum* botanically known as *Chrysanthemum morifolium*, and referred to by the cultivar name 'Festival Time Yellow Improved.'

'Festival Time Yellow Improved' identified as 20278-13A1 was discovered as a whole plant natural mutation in a controlled cultivated planting of the variety 'Festival Time Yellow' (unpatented seedling). The new variety 'Festival Time Yellow Improved' has been asexually reproduced by vegetative cuttings in Chichester, West Sussex, United Kingdom and the distinguishing characteristics are retained through successive generations of asexual reproduction.

BRIEF SUMMARY OF THE INVENTION

'Festival Time Yellow Improved' is a pot type of *Chrysanthemum* plant variety having a domed capitulum of golden yellow decorative flowers with an orange contrasting center.

Comparison with Parent

Plants of the new *Chrysanthemum* variety 'Festival Time Yellow Improved' are similar to the parent variety 'Festival Time Yellow' in plant habitat and growth rate. In side-by-side comparisons in Chichester, West Sussex, United Kingdom, under commercial practice, plants of the new *Chrysanthemum* variety 'Festival Time Yellow Improved' compared to plants of the parent 'Festival Time Yellow' in the following characteristics:

1. The new variety 'Festival Time Yellow Improved' produces golden yellow decorative flowers with a dark contrasting center whereas the parent 'Festival Time Yellow' produces yellow decorative flowers.
2. Plants of the new variety 'Festival Time Yellow Improved' have similar inflorescence to plants of the parent 'Festival Time Yellow.'

Comparison with Other Varieties

Plants of the new *Chrysanthemum* variety 'Festival Time Yellow Improved' are dissimilar to the cultivar 'Jose Sunset Lady' (U.S. Plant Pat. No. 10,800) in plant habitat and growth rate. In side-by-side comparisons in Chichester, West Sussex, United Kingdom, under commercial practice, plants of the new *Chrysanthemum* variety 'Festival Time Yellow Improved' differed from plants of the variety 'Jose Sunset Lady' in the following characteristics:

1. The new variety 'Festival Time Yellow Improved' produces golden yellow decorative flowers with an orange center whereas 'Jose Sunset Lady' produces yellow decorative flowers with a red center.
2. Plants of the new variety 'Festival Time Yellow Improved' have larger and shorter inflorescence than plants of 'Jose Sunset Lady.'

3. The plants of the new variety 'Festival Time Yellow Improved' have a quicker response than the plants of the variety 'Jose Sunset Lady.'

BRIEF DESCRIPTION OF ILLUSTRATIONS

Typical specimens of the plant and flowers for the new *Chrysanthemum* variety 'Festival Time Yellow Improved' are shown in the accompanying digital photograph. The colors shown are as true as possible within the usual limits of this kind of illustration.

FIG. 1 is a whole plant view of the new variety 'Festival Time Yellow Improved' grown in a pot. The plant shown in the illustration is 60 days from the commencement of short days.

DETAILED BOTANICAL DESCRIPTION

The following description of the new *Chrysanthemum* variety 'Festival Time Yellow Improved' is of plants grown in a greenhouse in Chichester, West Sussex, United Kingdom in the month of September. The cultivar has not been observed under all possible environmental conditions. The phenotype may vary significantly with variations in the environment such as temperature, length of day and light intensity, without any variance in genotype. The commercial classification of the new variety is a pot *Chrysanthemum.*

Plants of the new variety have been grown successfully under temperature conditions averaging about 19° C. at night and about 17° C. to 24° C. during the day under light conditions of about 5,000 to 6,000 foot candles. The plants respond well to the use of growth retardant, such as one B9 treatment at about 2 gram per liter. To produce a commercial product the plants may be pinched once with the center bud removed. The typical container size for commercial growth is 1 liter. It has been observed that the shelf life of the new variety is about 21 days with a response time of about 8 weeks. The new variety is suitable for growth in a temperature range of 15° C. to 25° C.

The new variety may be produced as a (spray or disbud). The following description is with respect to a plant produced as pot. In the description of this new *Chrysanthemum* variety, color values have been taken from The Royal Horticultural Society Colour Chart (R.H.S.C.C.).

Plant

Plant type: Pot.
Habit: Upright and free branching.
Height (cm): 18.
Width (cm): 27.
Stem:
- *Length* (*cm*).—5.
- *Diameter* (cm).—0.7.
- *Texture*.—Slightly pubescent.
- *Color*.—147B.

Branching characteristics: Upright and free branching.
Lateral branches:
- *Length* (*cm*).—10.
- *Diameter* (*cm*).—0.5.
- *Texture*.—Slightly pubescent.

Number of breaks from pinch: 5.
Response time: 54 days.
Vigor: Medium.
Shelf life: 21 days.
Disease (susceptibility/resistance observed): None observed to date.
Pest (susceptibility/resistance observed): None observed to date.
Drought and temperature (susceptibility/resistance observed): None observed to date.
Growth retardant type and treatment: 3 applications of 2.5 gm/liter B9 @ 2, 21 and 28 days after sticking unrooted cuttings.

The plants were grown for 2 weeks in Long Day conditions (20 hours of light) and then transferred to Short Day conditions (13 hours of dark).

Propagation:
- *Type*.—Vegetative Propagation Via Stem Cuttings.
- *Time to rooting*.—14 days with soil temperatures of 18° C.
- *Rooting habit*.—After 7 days the first roots emerge and form root primordia. In 14 long days a complete root system is developed.

Foliage

Number of leaves per lateral branch: 10.
Compound or single: Single.
Arrangement of leaves: Alternate.
- *Shape of leaf*.—5 lobed ovate.
- *Size of leaf*.—Width (cm): 4 Length (cm): 7.
- *Leaf apex*.—Acute.
- *Base*.—Obtuse.
- *Attachment*.—Petioled.
- *Aspect*.—Slightly undulating.
- *Margin*.—Palmately lobed.
- *Surface characteristics*.—Top: slightly pubescent. Bottom: pubescent.

Petiole:
- *Color*.—137B.
- *Length* (*cm*).—0.8.
- *Diameter* (*cm*) .—0.2.

Venation:
- *Color*.—Upper side: 147B. Under side: 147B.

Color:
- *Mature leaf, upper side*.—137A; under side: 137C.
- *Young leaf, upper side*.—137A; under side: 137C.

Flower

Flower appearance: Matte.
Flower type: Decorative.
Flower form: Slightly domed.
Flower shape: Circular.
Flowering habit: Cyme.
Number of blossoms per branch: 5.
Typical and observed flowering season: January to December.
Inflorescence form: Cyme.
- *Depth of fully expanded blossoms* (*cm*).—2.5.
- *Diameter of fully expanded blossoms* (*cm*).—7.

Phyllaries:
- *Number*.—25.
- *Color*.—137A.
- *Length* (*cm*).—0.6 to 1.
- *Width* (*cm*).—0.2.
- *Texture/appearance*.—Pubescent.

Peduncle:
- *Length* (*cm*).—10.
- *Diameter* (*cm*).—0.5.
- *Angle from stem* (*degrees*).—10.
- *Color*.—137B.
- *Surface*.—Slightly pubescent.
- *Habit*.—Slightly undulating.
- *Strength*.—Medium.

Pedicel:
*Length*.—Terminal (cm): 4; lateral (cm): 6.
*Diameter* (*cm*).—0.3.
*Color*.—137B.
*Surface*.—Slightly pubescent.
*Habit*.—Slightly undulating.
*Strength*.—Medium.
Ray florets:
*Form/shape*.—Straight.
*Texture/appearance*.—Matte.
*Number per flower*.—200.
*Length* (*cm*).—2 Width (cm): 0.8.
*Apex*.—Slightly dentate.
*Base*.—Tapered.
*Margin*.—Entire.
Disc florets: No known disc florets.
Fragrance: None.
Flower bud (at onset of color):
*Length* (*cm*).—0.9.
*Diameter* (*cm*).—1.
*Form/shape*.—Globular.
General flower color:
*1. Ray florets, upper side*.—Immature: 10A and 26A. Mature: 10B and 26B. Older/Fading: 10B and 26B.
*2. Ray florets, under side*.—Immature: 26B. Mature: 22B. Older/Fading: 10C.
*3. Bud*.—26B.
Flower progression with age: There is a slight color fading and reflex of the petals with age.

Reproductive Organs

Gynoecium present on Ray florets.
Ray florets per individual flower. Pistillate.
*Pistil number*.—200.
*Stigma color*.—6C.
*Stigma shape*.—Forked.
*Style color*.—6C.
*Style length* (*cm*).—0.5.
Androecium: None observed.
Fruit and seeds: None observed.

What is claimed is:

1. A new and distinct variety of *Chrysanthemum* plant, substantially as described and illustrated herein.

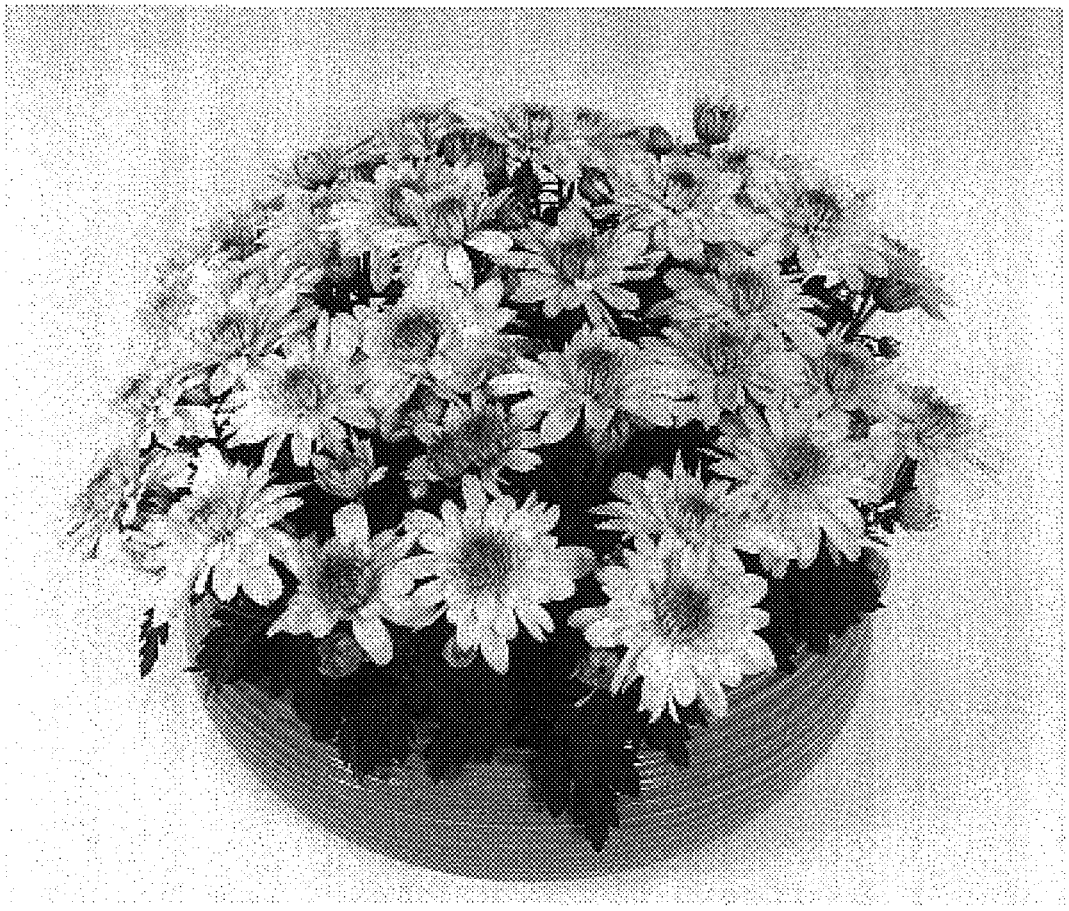

* * * * *